United States Patent
Messal et al.

(10) Patent No.: US 6,777,647 B1
(45) Date of Patent: Aug. 17, 2004

(54) COMBINATION LASER CUTTER AND CLEANER

(75) Inventors: Todd Messal, Orono, MN (US); Kenneth Merdan, Greenfield, MN (US); Vitaly Shapovalov, New Hope, MN (US); David Gilbert, St. Louis Park, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/418,253

(22) Filed: Apr. 16, 2003

(51) Int. Cl.[7] ............................................. B23K 26/00
(52) U.S. Cl. ........................... 219/121.84; 219/121.67; 219/121.68
(58) Field of Search ...................... 219/121.84, 121.85, 219/121.67, 121.68, 121.69

(56) References Cited

U.S. PATENT DOCUMENTS

| | | | |
|---|---|---|---|
| 3,619,550 A | 11/1971 | Matthews | 219/121 |
| 4,039,799 A | 8/1977 | Stumpf | 219/121 L |
| 4,288,680 A | 9/1981 | Röder | 219/232 LG |
| 5,073,694 A | 12/1991 | Tessier et al. | 219/121.7 |
| 5,222,617 A | 6/1993 | Gregory et al. | 219/121.7 |
| 5,421,955 A | 6/1995 | Lau et al. | 216/48 |
| 5,500,503 A | 3/1996 | Pernicka et al. | 219/121.64 |
| 5,514,154 A * | 5/1996 | Lau et al. | 623/1.15 |
| 5,632,840 A | 5/1997 | Campbell | 156/196 |
| 5,645,740 A | 7/1997 | Naiman et al. | 219/121.68 |
| 5,656,186 A | 8/1997 | Mourou et al. | 219/121.69 |
| 5,703,340 A | 12/1997 | Ohta et al. | 219/121.48 |
| 5,746,765 A | 5/1998 | Kleshinski et al. | 606/198 |
| 5,759,192 A | 6/1998 | Saunders | 606/194 |
| 5,766,238 A | 6/1998 | Lau et al. | 623/1 |
| 5,776,161 A | 7/1998 | Globerman | 604/194 |
| 5,780,807 A | 7/1998 | Saunders | 219/121.71 |
| 5,836,964 A * | 11/1998 | Richter et al. | 606/194 |
| 5,852,277 A | 12/1998 | Gustafson | 219/121.67 |
| 5,885,258 A | 3/1999 | Sachdeva et al. | 604/281 |
| 5,889,255 A | 3/1999 | Bogart et al. | 219/121.65 |
| 5,902,499 A | 5/1999 | Richerzhagen | 219/121.84 |
| 5,906,759 A | 5/1999 | Richter | 219/121.63 |

(List continued on next page.)

FOREIGN PATENT DOCUMENTS

| | | | |
|---|---|---|---|
| EP | 1139415 A1 * | 10/2001 | H01L/21/68 |
| WO | 89/03274 | 4/1989 | |
| WO | 01/75966 A1 | 10/2001 | |

*Primary Examiner*—M. Alexandra Elve
(74) *Attorney, Agent, or Firm*—Crompton, Seager & Tufte LLC (57) ABSTRACT

A system for processing a work piece comprises a laser jet mechanism having a laser and a fluid source. The laser is constructed and arranged to transmit laser energy to the work piece and the fluid source is constructed and arranged to direct a fluid stream to the work piece. The laser energy is transmitted to the work piece through the fluid stream. The fluid stream comprises at least one processing solution selected from the group consisting of: at least one etchant, at least one abrasive, at least one polish, at least one cleaner, at least one detergent and any combination thereof. The fluid stream optionally comprises water.

34 Claims, 4 Drawing Sheets

U.S. PATENT DOCUMENTS

| | | | |
|---|---|---|---|
| 5,907,893 A | 6/1999 | Zadno-Azizi et al. | 29/6.1 |
| 5,922,005 A | 7/1999 | Richter et al. | 606/192 |
| 5,935,162 A * | 8/1999 | Dang | 623/1.15 |
| 5,994,667 A | 11/1999 | Merdan et al. | 219/121.67 |
| 6,019,784 A | 2/2000 | Hines | 623/1 |
| 6,080,191 A | 6/2000 | Summers | 623/1.22 |
| 6,131,266 A * | 10/2000 | Saunders | 29/557 |
| 6,160,240 A | 12/2000 | Momma et al. | 219/121.85 |
| 6,197,048 B1 | 3/2001 | Richter | 623/1.15 |
| 6,240,616 B1 | 6/2001 | Yan | 29/527.2 |
| 6,295,714 B1 | 10/2001 | Roychowdhury et al. | 29/516 |
| 6,316,743 B1 | 11/2001 | Nagahori et al. | 219/121.67 |
| 6,327,772 B1 | 12/2001 | Zadno-Azizi et al. | 29/557 |
| 6,345,057 B1 | 2/2002 | Ben-Eli | 370/513 |
| 6,369,355 B1 | 4/2002 | Saunders | 219/121.71 |
| 6,521,865 B1 | 2/2003 | Jones et al. | 219/121.72 |
| 2002/0087209 A1 * | 7/2002 | Edwin et al. | 623/1.11 |
| 2003/0045031 A1 * | 3/2003 | Kobayashi | 438/113 |
| 2003/0062126 A1 * | 4/2003 | Scaggs | 156/345.26 |

\* cited by examiner

COMBINATION LASER CUTTER AND CLEANER

CROSS-REFERENCE TO RELATED APPLICATIONS

Not Applicable

STATEMENT REGARDING FEDERALLY SPONSORED RESEARCH

Not Applicable

BACKGROUND OF THE INVENTION

A stent is a radially expandable endoprosthesis which is adapted to be implanted in a body lumen. Stents are typically used in the treatment of atherosclerotic stenosis in blood vessels and the like to reinforce body vessels and to prevent restenosis following angioplasty in the vascular system. They have also been implanted in urinary tracts, bile ducts and other bodily lumen. They may be self-expanding or expanded by an internal radial force, such as when mounted on a balloon.

Delivery and implantation of a stent is accomplished by disposing the stent about a distal portion of the catheter, percutaneously inserting the distal portion of the catheter in a bodily vessel, advancing the catheter in the bodily lumen to a desired location, expanding the stent and removing the catheter from the lumen. In the case of a balloon expandable stent, the stent is mounted about a balloon disposed on the catheter and expanded by inflating the balloon. The balloon may then be deflated and the catheter withdrawn. In the case of a self-expanding stent, the stent may be held in place on the catheter via a retractable sheath. When the stent is in a desired bodily location, the sheath may be withdrawn allowing the stent to self-expand.

In the past, stents have been generally tubular but have been composed of many configurations and have been made of many materials, including metals and plastic. Ordinary metals such as stainless steel have been used as have shape memory metals such as Nitinol and the like. Stents have also been made of bio-absorbable plastic materials. Stents have been formed from wire, tube stock, etc. Stents have also been made from sheets of material which are rolled.

A number of techniques have been suggested for the fabrication of stents from sheets and tubes. One such technique involves laser cutting a pattern into a sheet of material and rolling the sheet into a tube or directly laser cutting the desired pattern into a tube. Other techniques involve cutting a desired pattern into a sheet or a tube via chemical etching or electrical discharge machining.

Laser cutting of stents has been described in a number of publications including U.S. Pat. No. 5,780,807 to Saunders, U.S. Pat. No. 5,922,005 to Richter and U.S. Pat. No. 5,906,759 to Richter. Other references wherein laser cutting of stents is described include: U.S. Pat. Nos. 5,514,154, 5,759,192, 6,131,266 and 6,197,048.

A typical laser cutting system relies on a laser to produce a beam which is conditioned as necessary via an optical unit and focused into a spot beam which is impinged against a hollow tube that is to become the stent. The hollow tube may be moved via a rotational motor drive and linear motion drive.

An example of a conventional laser for cutting a stent is a highly focused pulsed Nd:YAG laser which has a pulse duration in the range of approximately 0.1 to about 2.0 milliseconds. This is a long pulse time for cutting and characteristically produces a relatively large melt zone and heat affected zone (HAZ) on the metal. The conventional laser cutting process may result in the formation of melt dross and/or other debris forming on the cut tube.

In a more recent development, cutting and processing systems have been developed that incorporate a water column and laser such as is described in international publication number WO 01/75966 to SYNOVA Inc., of Lausanne, Switzerland. Such a system employs a laser-microjet that uses a laser beam contained within a waterjet as a parallel beam, similar in principle to an optical fiber achieved by a high index of refraction between fluid and air and/or inert atmosphere. While the use of water in a water/laserjet hybrid system may aid in preventing the formation and buildup of excess debris on the object being cut, an object, such as a tube being cut for use as an implantable medical device, cut in this manner will still require further cleaning and/or polishing processes prior to use.

In light of the above, a need exists to provide a medical device processing method and system wherein the processes of laser cutting, etching, cleaning and/or polishing of an object are combined into a reduced number of processes or steps, or in some embodiments a single process or step.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is directed to a variety of embodiments. As indicated above, the use of a hybrid laser/water jet for the purpose of cutting is known. In embodiments of the present invention however, a novel type of laser/fluid jet mechanism is described wherein the use of water as a laser transmission media is supplanted or supplemented with a processing fluid such as one or more etchants, abrasives, polishes, cleaners, detergents, etc.

In the various embodiments of the invention, a processing fluid is suitable for transmission of laser energy therethrough without causing significant disruptive affect on the laser energy being transmitted. As a result the processing fluid through which the laser energy is directly transmitted must have a high transparency in order for the laser wavelength to be transparent.

In at least one embodiment the work piece is a hollow tube of a material suitable for constructing a stent. Such a tube may be at least partially constructed from, stainless steel, nickel, titanium, palladium, gold, tantalum, or any other metal or alloy, such as nitinol, thereof suitable for constructing a stent. In at least one embodiment the tube is at least partially constructed from a polymer substance.

In at least one embodiment the hollow tube is a tube of material suitable for constructing a tubular medical device, or component thereof. In such an embodiment the processed tube may be utilized as, or a portion of: a hypotube, a catheter, a balloon, a sock, a sleeve, an embolic protection filter, etc.

In at least one embodiment the laser energy is transmitted to the work piece in a column of fluid, wherein the column of fluid transmitting the laser energy is within one or more additional columns of fluid. The laser transmission column may comprise a fluid that is different than the fluid of the adjacent or additional columns. For example the transmission column of fluid may comprise water, while one or more other columns of fluid may comprise one or more processing fluids, such as etchants, abrasives, polishes, detergents, cleaners, etc. In another example the transmission column comprises a solution of one or more processing fluids whereas an adjacent column or columns may comprise water and/or other fluid.

In the various embodiments described herein the fluid selected to transmit laser energy to the work piece must have a high transparency for the wavelength of the laser energy to be transmitted therethrough. It is necessary that the fluid through which the laser energy is transmitted is suitable to prevent significant optical loss or degradation of the laser energy transmitted therethrough.

In some embodiments one or more of the columns of fluid apply ultrasonic energy to the work piece. In some embodiments, one or more fluid columns are transmitted to the work piece at a frequency of about 20 KHz to about 40 KHz or greater frequency. In some embodiments the frequency is about 1 MHz or greater. In some embodiments the frequency is fixed, random, varying, cyclic and/or any combination thereof. In at least one embodiment, wherein multiple columns are applied to the work piece, different columns are applied to the work piece at different frequencies.

In at least one embodiment the processing fluid is a solution of at least one etchant, abrasive, polish, cleaner, detergent, etc. in combination with water.

In at least one embodiment the processing fluid comprises glycerin.

In at least one embodiment the processing fluid comprises fluorinated alcohol.

In at least one embodiment at least one column of fluid is a processing fluid such as fluorinated base etchant in combination with sulfates and/or peroxides and/or water, such as for example $HF+H_2SO_4+H_2O_2+H_2O$. In at least one embodiment, the solution of $HF+H_2SO_4+H_2O_2+H_2O$ is provided at a ratio of 30/30/1/39.

In at least one embodiment at least one column of fluid comprises a fluid selected from the group comprising: a solution sodium hydroxide and water; a solution of ammonium bifluorite and water; a solution of fluoboric, nitric and water; a solution of hydrochloric acid and acetic acid; a solution of one or more non fluorinated etchants, and hydrogen peroxide; a solution of hydrofluoric, nitric and water; citric acid and any combination thereof.

In at least one embodiment the laser energy directed to the work piece is transmitted from a laser. The laser may be any type of laser including but not limited to diode lasers, YAG lasers, UV lasers, IR lasers, $CO_2$ lasers, etc.

In some embodiments the laser energy and at least one column of fluid define a beam size or diameter, at a point of intersection on the work piece, of about 5 to about 120 microns or greater. In at least one embodiment the beam size is about 35 to about 60 microns.

In some embodiments the column of fluid comprises an electrolytic solution.

In some embodiments the column of fluid may be directed through manipulation of the fluid's magnetic field.

In some embodiments the direction of the column of fluid may be deflected by manipulation of electrostatic forces. In at least one embodiment the column of fluid is passed by one or more electrostatic deflectors which are constructed and arranged to bend the fluid column in a desired manner around the surface of the deflector.

In some embodiments fluid is passed through a heating and/or a cooling mechanism prior to forming the fluid into a column.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 1:
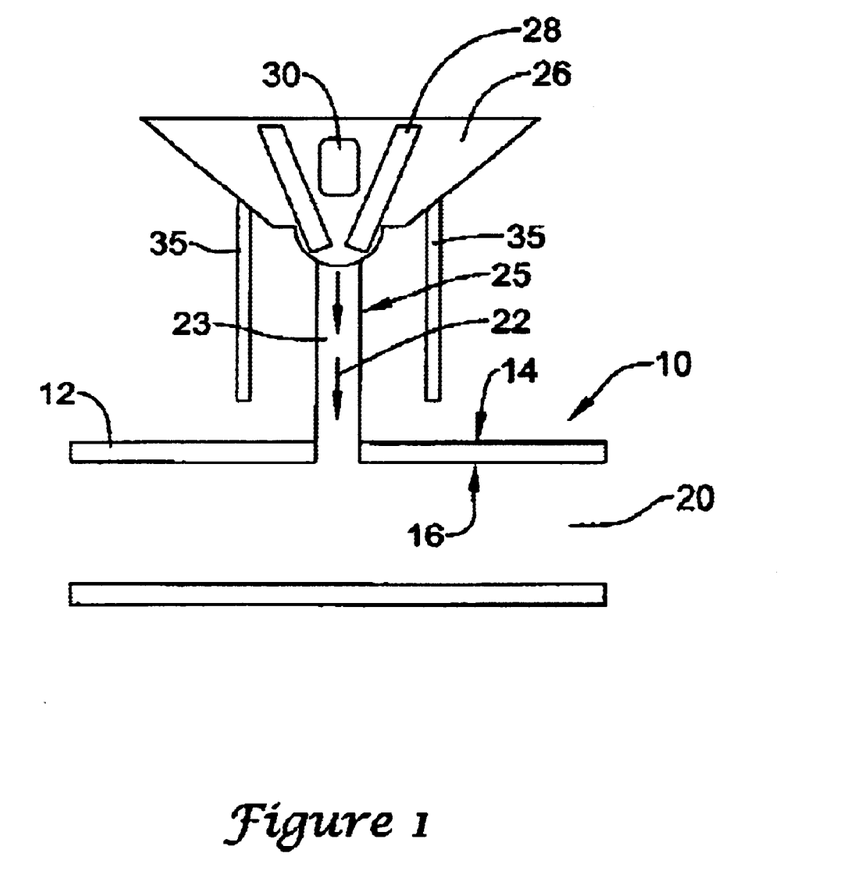
FIG. 1 is a cross-sectional side view of an embodiment of the invention.

As indicated above the present invention is directed to a variety of embodiments. In at least one embodiment the invention is directed to a system for processing and/or cutting a work piece 10 such as is shown in FIG. 1. Work piece 10 may be a sheet of material, a hollow tubular body, or any other object having a surface that requires cutting, etching, etc.

Figure 2:
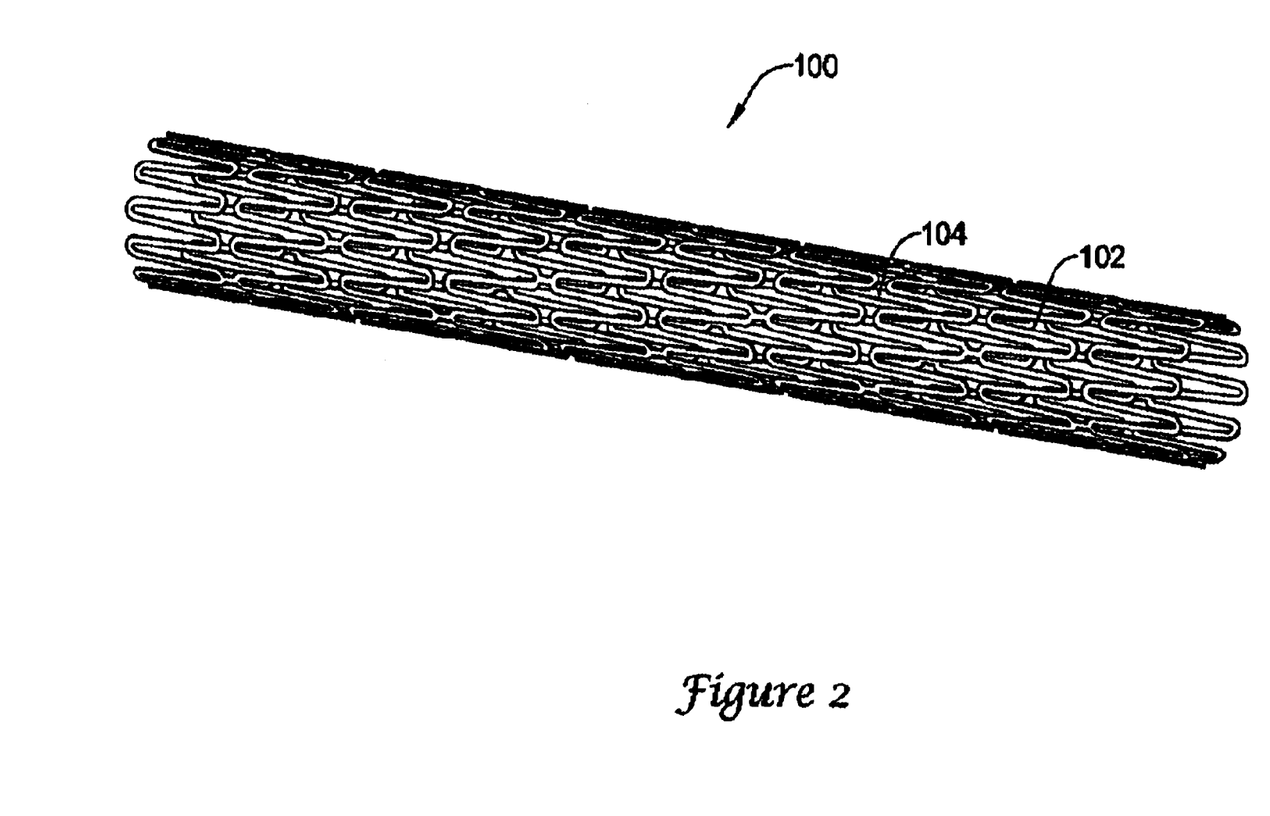
FIG. 2 is a perspective view of a stent manufactured in accordance with an embodiment of the invention.

For purposes of illustration, in the embodiment shown the work piece 10 is illustrated as a hollow tubular body constructed of a material that is subject to laser processing and/or cutting. Such a tube 10 may be a tubular member suitable for the construction of a stent, graft, stent-graft, vena cava filter, or other device suitable for implantation into a body lumen. Such devices are herein collectively referred to as stents and an example of a stent is shown generally at reference numeral 100 in FIG. 2. The exemplary stent 100 shown in FIG. 2 comprises a pattern of interconnected stent members 102 which define one or more spaces 104 therebetween. Material is removed from the tube 10 of FIG. 1 to provide the resulting stent 100 with the pattern of members 102 and spaces 104 shown. As indicated the particular pattern of members 102 and spaces 104 provided to the stent 100 shown in FIG. 2 represents merely one of an infinite variety of stent patterns that may be cut into the tube 10 according to the processes described herein.

Where the tube 10 is intended for the construction of a stent, the tube 10 will typically be at least partially constructed from a metal such as stainless steel, nickel, titanium, palladium, gold, tantalum, or any other metal, metal-oxide or alloy thereof. In some embodiments the tube 10 may be comprised of multiple layers of material. For example the tube 10 may be at least partially constructed of stainless steel, and/or nitinol, and have one or more layers of gold or other material, such as including iridium oxide, etc., applied thereon. In at least one embodiment tube 10 is constructed of a nickel-titanium alloy such as nitinol or other shape-memory alloys or materials.

In some embodiments at least a portion of tube 10 may by platinum enriched such as by including a dispersion of platinum within/upon the base material of the tube 10. In at least one embodiment the tube 10 is constructed from about 30 percent platinum or other radiopaque metal.

In some embodiments, tube 10 may be a tubular member suitable for use in the manufacture of a catheter or portion(s) thereof. In such applications, the tube 10 will typically be constructed at least partially from one or more polymer substances including, but not limited to: polyester/polyether elastomers such as Arnitel™ available from DSM Engineering; polyurethane-polyether polymers, such as Tecothane™ and/or Tecoplast™ both being available from Thermedics, Inc.; polyester-polyurethanes, such as Pellethane™ sold by Dow Chemical; polyester-polyurethanes, such as Estane™ sold by BF Goodrich; polyether block amides (PEBA), such as Pebax™ available from Elf Atochem; styrene-butadien-styrene triblock copolymers, such as Kraton™ sold by Shell Chemical company; styrenic block copolymers; polyurethanes; silicone rubber; natural rubber; copolyesters; polyamides; EPDM rubber/polyolefin; nitril rubber/PVC; fluoroelastomers; butyl rubber; epichlorohydrin; block copolymers; polyethylene terephthalate (PET); polyethylene naphthalate (PEN); polybutylene terephthalate (PBT); poly-trimethylene terephthalate (PTT); poly lactic acid (PLA); fluoropolymers; polyolefins; polystyrene; polyvinyl chloride (PVC); acrylonitrile-butadiene-styrene polymers; polyacrylonitrile; polyacrylate, vinyl acetate polymer; cellulose plastics; polyacetal; polyethers; polycarbonates; polyphenylene sulfide; polyarylethersulfones;

polyaryletherketones; polytetrafluoroethylene; polyamide copolymer, such as MXD6™ available from Mitsubishi Gas Chemical Co. or Cristamid™ available from Atofina; shape-memory polymers; liquid crystal polymers; bio-absorbable polymers; radiopaque polymers; MRI-visible polymers; etc.

Tube 10 may also include various coatings or surface materials, such as drug and/or drug vectors, lubricants, etc.

In some embodiments the tube 10 and/or one or materials from which the tube is constructed is bioresorbable.

Regardless of the particular composition or the type of material used for tube 10, the tube comprises a tube wall 12 having an external surface 14 and an interior surface 16. The interior surface 16 of the tube wall 12 define a passage or lumen 20.

In practice, at least a portion of the tube wall 12 is cut or otherwise modified by applying laser energy, indicated by arrow 22, to the external surface 14 of the tube 10. A space 104 may be provided to the tube wall 12 by allowing the laser energy 22 to heat and/or ablate selected portions of the tube wall 12. The space 104 may extend from the exterior surface 14 to the interior surface 16 or only partially through the tube wall 12 as desired or determined by a predetermined pattern.

The laser energy 22 is transmitted to the tube wall 12 through a stream of fluid hereinafter referred to as a fluid stream 23. Fluid stream 23 behaves similarly to a fiber optic in that the fluid stream 23 allows the laser energy 22 to be transmitted and/or focused therethrough.

The combined laser energy 22 and fluid stream 23 is collectively referred to herein as a jet 25.

As indicated above, the fluid stream 23 may comprise one or more processing fluids such as one or more etchants, abrasives, polishes, cleaners, detergents, etc. A processing fluid has a transparency which substantially allows the wavelength of the laser energy to be transmitted therethrough. Some examples of suitable processing solutions which may comprise the fluid stream 23 include but are not limited to: organic solvents, chemical detergents having hydrophilic and hydrophobic regions; glycerin; fluorinated alcohol; one or more fluorinated base etchants in combination with sulfates and/or peroxides and/or water, such as for example $HF+H_2SO_4+H_2O_2+H_2O$ at a ratio of 30/30/1/39, for example; a solution sodium hydroxide and water; a solution of ammonium bifluorite and water; a solution of fluoboric, nitric and water; citric acid; a solution of hydrochloric acid and acetic acid; a solution of one or more non fluorinated etchants and hydrogen peroxide; a solution of hydrofluoric, nitric and water; an electrolytic solution and any combinations thereof.

By providing a jet 25 with a fluid stream 23 comprised of one or more processing fluids in addition to or rather than water alone, the efficiency of tube cutting and stent manufacturing processes are improved, and/or the number of processing steps reduced, as the cutting, etching, abrading, polishing and cleaning steps may all be incorporated into the combined cutting process described herein.

Where the tube 10 is to be processed into a stent, the tube 10 is rotated and/or repositioned to allow portions of the entire tube wall 12 to be eventually cut or otherwise processed. Similarly, where the tube is a hypotube the tube 10 may be positioned and/or moved to allow for one or more regions of the external surface 14 of the tube 10 to be processed by the jet 25. As indicated above, regardless of the type of tube 10, in some applications the laser energy 22 of the jet 25 may be applied to mark, cut, drill through or otherwise process one or more portions of the tube wall 12.

As is shown in FIG. 1 jet 25 is directed to the exterior surface 14 of the tube wall 12. Jet 25 is supplied by a laser-jet mechanism 26 which comprises a fluid source 28 and a laser energy source or laser 30.

Laser 30 may be any class of laser desired, such as including but not limited to: gas, diode, and solid-state classes of lasers. Some specific examples of suitable laser types include but are not limited to: YAG, IR, UV, $CO_2$, diode, visible light, Excimer, etc., as well as any combinations thereof Laser 30 may have a pulsed, CW and/or other operating mode or modes.

The fluid source 28 is constructed and arranged to direct a stream of fluid 23 toward the tube 10 and the laser 30 is constructed and arrange to transmit the laser energy 22 through the fluid stream 23 toward the tube 10. The combined fluid stream 23 and laser energy 22 form the jet 25 which cuts the tube wall 12. Because the fluid stream 23 comprise one or more processing fluids as described above, the jet 25 while acting to cut the wall 12 of the tube 10 also may be utilized to etch, abrade, polish, clean, rinse, and cool the tube 10 simultaneously.

Figure 3:
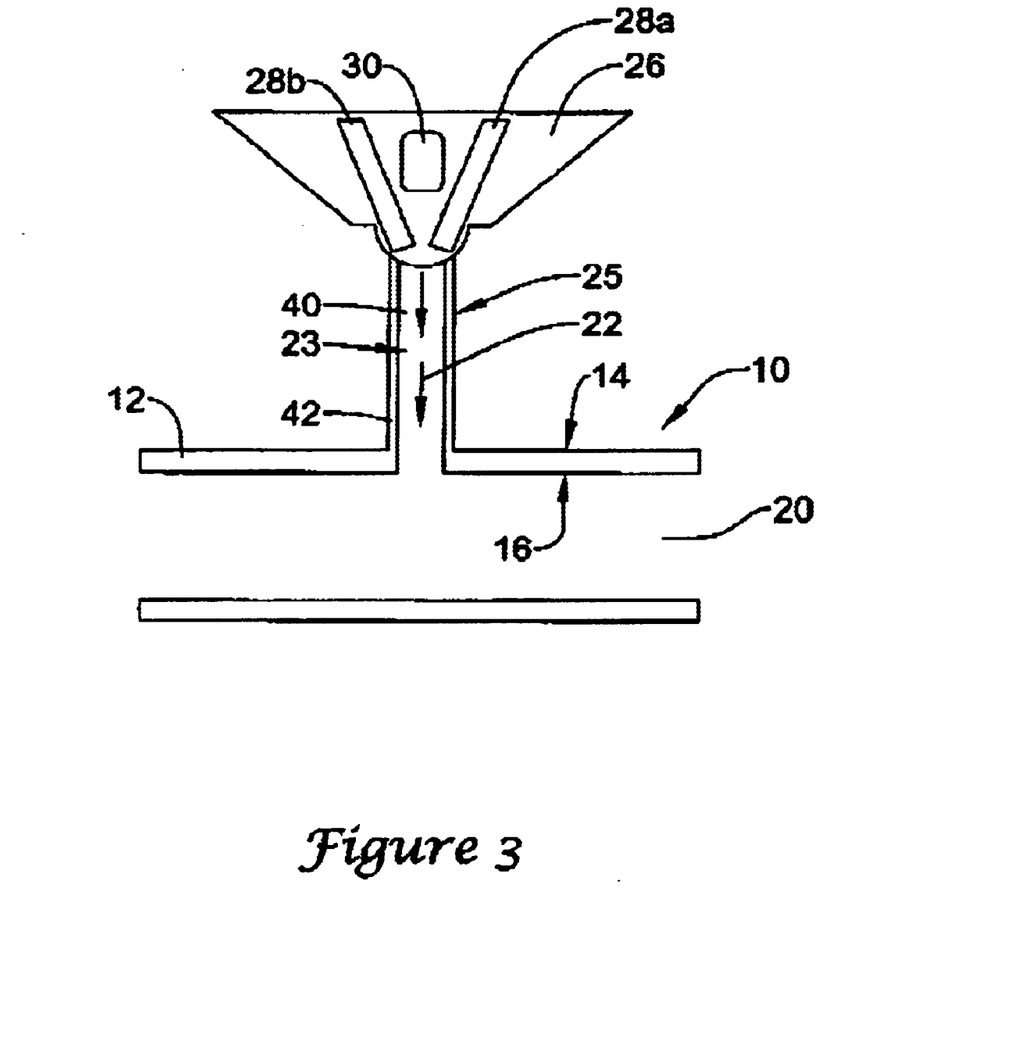
FIG. 3 is a cross-sectional side view of the embodiment shown in FIG. 1 wherein the fluid stream comprises a plurality of fluid columns.

In at least one embodiment, such as for example in the embodiment shown in FIG. 3, the fluid stream 23 defines a plurality of fluid columns, such as are represented by a first column 40 and a second column 42, though it is understood that any number of columns over one may be utilized. In some embodiments multiple columns are coaxially or sequentially transmitted.

In the embodiment shown in FIG. 3 the first or center column 40 acts to directly transmit the laser energy 22 in the manner such as has been previously described. The center column 40 may be any type of processing or laser transmission fluid desired. Desirably, the column through which laser energy 22 is transmitted, such as for example fluid column 40, comprises a fluid transparent to which the wavelength of the laser energy to be transmitted therethrough is transparent. Fluid columns adjacent to and/or surrounding the center column 40, such as fluid column 42 which are not utilized to directly transmit laser energy 22, are not required to have optical properties necessary to prevent disruption to the laser energy 22. As a result, fluid columns, as represented by column 42 that is not utilized for direct transmission of laser energy 22, may have a variety of properties different than those of the center column 40. For example, where the center column 40 comprises water, or even a solution of water and one or more fluid processing solutions, one or more adjacent fluid columns 42 may comprise a processing solution having different viscosity or other properties such as temperature, transparency, vapor pressure, index of refraction, thermo-conductivity, electro-resistivity, etc. In some embodiments, column 42 may comprise one or more particulate abrasives or polishes.

Though the fluid comprising each column 40 and 42 may be the same, where the columns 40 and 42 comprise different fluids a separated fluid source 28a and 28b may supply the respective fluids.

In at least one example, the center column 40 may comprise a solution of one or more processing fluids while the adjacent column(s) comprise water and/or other fluids. In some embodiments laser energy may be passed through the second or outer fluid column 42.

In some embodiments, the fluid source 28 is constructed and arranged to pulse one or more of the columns of fluid 40 and 42 and/or the entire fluid stream 23 at an ultrasonic frequency. In some embodiments the frequency at which the one or more columns 40 and 42, are pulsed is about 40 KHz. In some embodiments one or more columns 40 and 42 are pulsed at about 20 KHz to about 40 KHz. In some embodiment one or more of the columns 40 and 42 are pulsed at a frequency of about 1 MHz or greater. In at least one embodiment, wherein multiple fluid columns, such as fluid columns 40 and 42, are applied to the tube 10, the different columns 40 and 42 are applied to the tube 10 at different frequencies. The frequency of the fluid pulses may be varied.

Figure 4:
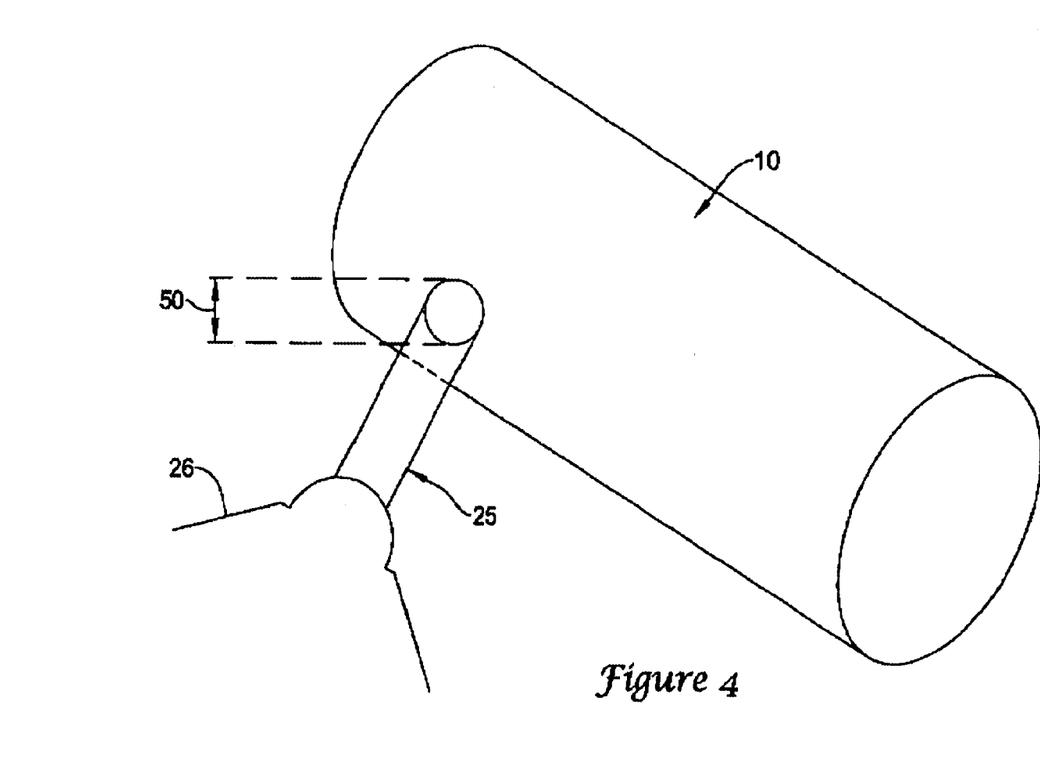
FIG. 4 is a partial perspective view of the embodiment shown in FIG. 1 illustrating the diameter of the jet.

As shown in FIG. 4, in some embodiments the jet 25 defines a jet size or diameter 50, at a point of intersection on the tube 10, of about 5 to about 120 microns. In at least one embodiment the jet diameter is about 35 to about 60 microns.

In some embodiments, the laserjet mechanism such as is shown in FIG. 1 may further include one or more moveable magnetic guide plates 35. The jet 25 is passed through or adjacent to one or more of the magnetic guide plates 35. The magnetic guide plates 35 are constructed and arranged to affect the magnetic field of the fluid stream 23 thereby allowing the jet 25 to be moved or redirected by selectively manipulating or moving the guide plates 35 in a desired direction.

In at least one embodiment the guide plates may be electrostatically charged in addition to or instead of being magnetic. Where the guide plates 35 are electrostatically charged they may act to deflect or bend the path of the jet 25 around the surface of the deflector/guide plate 35. As the jet 25 is passed through or adjacent to one of more of the deflectors/guide plates 35 the jet 25 is bent toward the plate 35. by manipulating the proximity of the plate 35, the charge of the plate 35, and/or the electrostatic properties of the fluid stream 23 the jet 25 may be moved or directed to a variety of directions. As a result, the jet 25 may be directed to the tube 10 at a variety of angles as may be desired. Such redirection of the jet 25 allows a given area of the tube 10 to be cut from one or more sides. Providing such variable cutting directions and angles allows a strut 102, such as is shown in FIG. 2, to be provided with a variety of physical characteristics with relative ease. Such as fore example, a strut 102 may be cut in this manner in order to provide the strut 102 with a wider diameter at the inner diameter of the stent 100 than on the outer diameter of the stent or vice versa.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A system for processing a work piece comprising:
   a laser jet mechanism, the laser jet mechanism comprising a laser and a fluid source, the laser constructed and arranged to transmit laser energy to the work piece, the fluid source constructed and arranged to direct a fluid stream of at least one processing solution to the work piece, the laser energy being transmitted to the work piece through the fluid stream, the at least one processing solution is selected from the group consisting of: at least one etchant, at least one abrasive, at least one polish, at least one detergent and any combination thereof.

2. The system of claim 1 wherein the work piece comprises a sheet of material.

3. The system of claim 1 wherein the work piece comprises a hollow tubular member of material defined by a tube wall and defining a lumen therethrough.

4. The system of claim 3 wherein the fluid stream in combination with the laser energy forms a cutting jet, the cutting jet constructed and arranged to at least partially remove at least one predetermined area of material from the tube wall.

5. The system of claim 3 wherein the fluid stream in combination with the laser energy forms a cutting jet, the cutting jet constructed and arranged to melt at least one predetermined area of material from the tube wall.

6. The system of claim 4 wherein by removing the at least one predetermined area of the material from the tube results in the tube defining a plurality of spaced apart interconnected members of the material.

7. The system of claim 6 wherein the plurality of spaced apart interconnected members of the material define a stent.

8. The system of claim 3 wherein the tube is at least partially constructed from at least one metal of the group consisting of: stainless steel, nickel, titanium, palladium, gold, tantalum, and their alloys or combinations thereof.

9. The system of claim 3 wherein the tube is at least partially constructed form at least one shape-memory material.

10. The system of claim 3 wherein the tube is at least partially constructed from at least one polymer material.

11. The system of claim 1 wherein the fluid stream has a transparency which allows a wavelength of the laser energy to be transmitted therethrough.

12. The system of claim 1 wherein the at least one processing solution is selected from the group consisting of: glycerin; fluorinated alcohol; one or more fluorinated base etchants; a solution sodium hydroxide and water; a solution of ammonium bifluorite and water; a solution of fluoboric, nitric and water; a solution of hydrochloric acid and acetic acid; a solution of one or more non fluorinated etchant and hydrogen peroxide; a solution of hydrofluoric, nitric and water; citric acid; an electrolytic solution and any combinations thereof.

13. The system of claim 4 wherein the cutting jet is constructed and arranged to polish at least a portion of the tube wall.

14. The system of claim 4 wherein the cutting jet is constructed and arranged to clean at least a portion of the tube wall.

15. The system of claim 4 wherein the cutting jet is constructed and arranged to rinse at least a portion of the tube wall.

16. The system of claim 1 wherein the laser is a selected from at least one member of the group consisting of: a YAG laser, an IR laser, a UV laser, a CO2 laser, a diode laser, Excimer laser, visible light laser, and any combination thereof.

17. A system for processing a work piece comprising:
a laser jet mechanism, the laser jet mechanism comprising a laser and a fluid source, the laser constructed and arranged to transmit laser energy to the work piece, the fluid source constructed and arranged to direct a fluid stream of at least one processing solution to the work piece, the laser energy being transmitted to the work piece through the fluid stream, the at least one processing solution is selected from the group consisting of: at least one etchant, at least one abrasive, at least one polish, at least one cleaner, at least one detergent and any combination thereof, the fluid stream optionally comprising water; and
wherein the fluid stream comprises a first fluid column and a second fluid column, the laser energy being transmitted to the work piece through the first fluid column, the first fluid column having a transparency which substantially corresponds to a wavelength of the laser energy transmitted therethrough, the second fluid column comprising the at least one processing solution.

18. The system of claim 17 wherein the first fluid column is at least partially contained within the second fluid column.

19. The system of claim 17 wherein the first fluid column is adjacent to the second fluid column.

20. The system of claim 17 wherein the second fluid column further comprising at least one particulate, the at least one particulate selected from the group consisting of: at least one particulate etchant, at least one particulate polish, at least one particulate abrasive.

21. The system of claim 17 wherein the fluid source is further constructed and arranged to allow at least one of the first fluid column and second fluid column to transmitted at an ultrasonic frequency.

22. The system of claim 21 wherein the laser is further constructed and arranged to transmit the laser energy at substantially the same frequency as the frequency of the at least one of the first fluid column and the second fluid column.

23. The system of claim 22 wherein at least one of the laser energy, the first fluid column and the second fluid column are excited to about 40 KHz.

24. The system of claim 22 wherein at least one of the laser energy, the first fluid column and the second fluid column are excited to about 20 KHz to about 40 KHz.

25. The system of claim 22 wherein at least one of the laser energy, the first fluid column and the second fluid column are excited to about 1 MHz or greater.

26. The system of claim 22 wherein the first fluid column and the second fluid column are pulsed at different frequencies.

27. A system for processing a work piece comprising: a laser jet mechanism, the laser jet mechanism comprising a laser and a fluid source, the laser constructed and arranged to transmit laser energy to the work piece, the fluid source constructed and arranged to direct a fluid stream of at least one processing solution to the work piece, the laser energy being transmitted to the work piece through the fluid stream, the at least one processing solution is selected from the group consisting of: at least one etchant, at least one abrasive, at least one polish, at least one cleaner, at least one detergent and any combination thereof, the fluid stream optionally comprising water; wherein the work piece comprises a hollow tubular member of material defined by a tube wall and defining a lumen therethrough;
wherein the fluid stream in combination with the laser energy forms a cutting jet, the cutting jet constructed and arranged to at least partially remove at least one predetermined area of material from the tube wall; and
wherein the cutting jet defines a jet diameter of about 5 to about 120 microns.

28. A system for processing a work piece comprising: a laser jet mechanism, the laser jet mechanism comprising a laser and a fluid source, the laser constructed and arranged to transmit laser energy to the work piece, the fluid source constructed and arranged to direct a fluid stream of at least one processing solution to the work piece, the laser energy being transmitted to the work piece through the fluid stream, the at least one processing solution is selected from the group consisting of: at least one etchant, at least one abrasive, at least one polish, at least one cleaner, at least one detergent and any combination thereof, the fluid stream optionally comprising water; wherein the work piece comprises a hollow tubular member of material defined by a tube wall and defining a lumen therethrough;

wherein the fluid stream in combination with the laser energy forms a cutting jet, the cutting jet constructed and arranged to at least partially remove at least one predetermined area of material from the tube wall; and wherein the cutting jet defines a jet diameter of about 35 to about 60 microns.

29. A system for processing a work piece comprising: a laser jet mechanism, the laser jet mechanism comprising a laser and a fluid source, the laser constructed and arranged to transmit laser energy to the work piece, the fluid source constructed and arranged to direct a fluid stream of at least one processing solution to the work piece, the laser energy being transmitted to the work piece through the fluid stream, the at least one processing solution is selected from the group consisting of: at least one etchant, at least one abrasive, at least one polish, at least one cleaner, at least one detergent and any combination thereof, the fluid stream optionally comprising water; wherein the work piece comprises a hollow tubular member of material defined by a tube wall and defining a lumen therethrough;

wherein the fluid stream in combination with the laser energy forms a cutting jet, the cutting jet constructed and arranged to at least partially remove at least one predetermined area of material from the tube wall; and wherein the laser jet mechanism further comprises at least one magnetic guide plate, the laser jet mechanism constructed and arranged to direct the cutting jet adjacent to the at least one magnetic guide plate, the at least one magnetic guide plate constructed and arranged to redirect the direction of the cutting jet by affecting a magnetic field of the cutting jet.

30. The system of claim 29 wherein the at least one magnetic guide plate is moveable, the direction of the cutting jet being redirected when the at least one magnetic guide plate is moved relative to the cutting jet.

31. A system for processing a work piece comprising: a laser jet mechanism, the laser jet mechanism comprising a laser and a fluid source, the laser constructed and arranged to transmit laser energy to the work piece, the fluid source constructed and arranged to direct a fluid stream of at least one processing solution to the work piece, the laser energy being transmitted to the work piece through the fluid stream, the at least one processing solution is selected from the group consisting of: at least one etchant, at least one abrasive, at least one polish, at least one cleaner, at least one detergent and any combination thereof, the fluid stream optionally comprising water; wherein the work piece comprises a hollow tubular member of material defined by a tube wall and defining a lumen therethrough;

wherein the fluid stream in combination with the laser energy forms a cutting jet, the cutting jet constructed and arranged to at least partially remove at least one predetermined area of material from the tube wall; and wherein the laser jet mechanism further comprises at least one electro-statically charged guide plate, the laser jet mechanism constructed and arranged to direct the cutting jet adjacent to the at least one guide plate, the at least one guide plate constructed and arranged to redirect the direction of the cutting jet by affecting at least one electrostatic property of the cutting jet.

32. The system of claim 31 wherein the at least one guide plate is moveable, the direction of the cutting jet being redirected when the at least one guide plate is moved relative to the cutting jet.

33. A method of manipulating a work piece comprises the following steps:

directing laser energy from a laser toward at least one point on the work piece;

applying a fluid stream of at least one processing solution from a fluid source to the at least one point on the work piece, the laser energy being transmitted to the at least one point on the work piece through the fluid stream, the fluid stream and the laser energy in combination forming a laser jet, the laser jet removing at least some quantity of material from the work piece in accordance with a predetermined pattern and the laser jet etching, abrading, or polishing the work piece.

34. The system of claim 1 wherein the fluid stream includes water.

* * * * *